June 6, 1944. P. L. KOVACH Plant Pat. 628

AVOCADO TREE

Filed Sept. 24, 1943

INVENTOR.
Paul L. Kovach
BY B. J. Craig.
ATTY.

Patented June 6, 1944

Plant Pat. 628

UNITED STATES PATENT OFFICE

628

AVOCADO TREE

Paul L. Kovach, Vista, Calif.

Application September 24, 1943, Serial No. 503,669

1 Claim. (Cl. 47—62)

This invention relates to a new and improved variety of avocado which has definite, highly desirable characteristics.

In the accompanying drawing.

Figure 1:
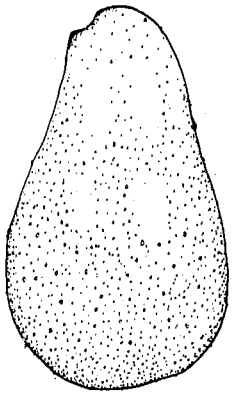
Fig. 1 is a side elevation of an avocado produced by the tree described herein.
Figure 2:
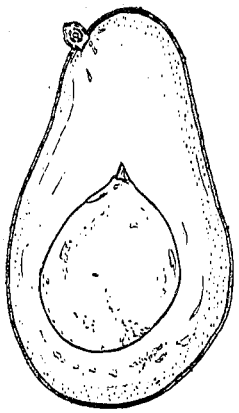
Fig. 2 is a sectional view through the avocado.
Figure 3:
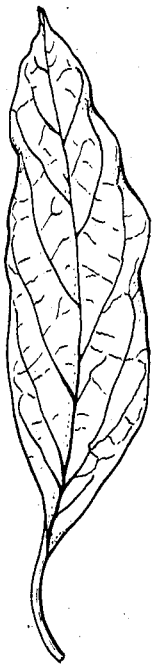
Fig. 3 is a top view of the leaf.
Figure 4:
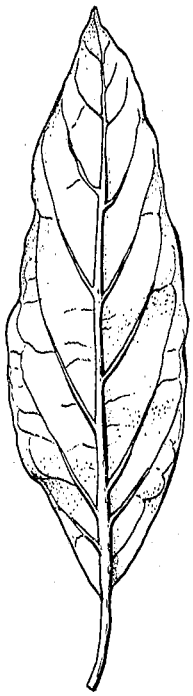
Fig. 4 is a bottom view of the leaf.

The original tree is a seedling of the Cantel variety. The seed was planted in 1921 in an avocado orchard located on Highland Avenue in Carlsbad, county of San Diego, California. The parent tree is dead. The tree wood is relatively close grained for an avocado and the tree, leaves and fruit successfully resist heavy winds.

The new variety has been successfully propagated on various types of seedlings as root stocks. The budwood, under proper care, grows rapidly. The budwood has a uniform dull green appearance and displays numerous slightly elevated dash shaped spots of a light green color. The number and prominence of these spots decreases as the wood hardens and when the wood reaches a diameter around one-half inch the spots disappear. The buds are of medium size, usually with two opposing bud scales which curve outwardly.

The tree usually blooms the second year after budding although, as is customary with avocados, the first set of buds is usually shed and the tree does not bear until the succeeding year.

The leaves when mature are rippled or sinuous along their edges. The average leaf is about ten inches long and two and three-quarters inches wide. The leaf veins, both principal and minor, are pronounced. The number of lateral veins is usually six although this varies.

The petiole of the mature leaf is one and three-quarters inches in length, generally with a slight curve. The freshly formed leaves are bronze and slightly fuzzy. As the leaf size increases the fuzziness and prominence of the principal veins decreases and may finally disappear. The surface color of a mature leaf is green but not glossy, the under surface of the mature leaf being grayish green. The mature leaves are straight or with a very slight curve adjacent the stem end.

The blossoms appear during the late spring after danger of frost has passed. The blossoms occur in large, loose, widely branching clusters and open over a comparatively short period. The fruit sets heavily within this short period although blossoming and fruit setting is influenced to some extent by weather conditions. The leaf drop during the blossoming season is light.

The fruit is evenly distributed on the tree and the tree does not over-bear. The fruit is pyriform in shape with a prominent neck and with the stem decidedly off center. The fruit is oblique at the base and apex, both ends are smoothly rounded and the fruit is without ribs or ridges.

The fruit is from five to five and a half inches in length, the greatest breadth being about two and three-quarters inches, and the diameter of the neck one and a half inches. The average weight is approximately eleven ounces. The fruit has an attractive elm green color with a glossy surface. The fruit is slightly less gray in color than the Fuerte.

The skin is smooth and medium thick, averaging approximately one to one and half mm. The skin peels readily and has small numerous greenish white flecks thereon which diminish somewhat in numbers towards the stem end. The skin cuts with barely perceptible grittiness.

The flesh of the outermost portion for approximately one-quarter inch is green, gradually fading to greenish yellow. The texture is buttery. The flesh fibres are perceptible but not prominent or tough. The flesh does not adhere to the seed.

The seed is somewhat tight in its cavity, has a smooth surface and weighs from one to one and a half ounces. The average length of the seed is approximately one and three-quarters inches and the average width about one and a half inches. The seed coat is chestnut brown in color, medium thick, and tight to the seed but separates clean. The average seed approximates 16% of the weight of the entire fruit and is nicely acorn shaped. The diameter of the basal end of the seed is eleven mm.

The fruit ripens from the middle of May to the middle of July or later, depending on location and climatic conditions.

The fruit does not appear in bunches, there generally being one fruit on a stem. The stem of the fruit averages about six inches in length and is tough and firmly attached to the fruit and will not snap off or lose its fruit in heavy winds.

My new variety differs from the Fuerte in that it has a decidedly offset stem as clearly shown in the drawing. It has an attractive glossy surface. The tree is not so pronounced a spreading type as the Fuerte. The budwood is dull green with minute, elevated, light green spots, whereas the budwood of the Fuerte displays numerous reddish dashes of unequal length which are not elevated. This new variety of avocado blossoms in late spring; while the Fuerte blossoms in early spring and all too often throughout the winter.

My avocado differs from the Ryan by its smooth, glossy appearance. The Ryan has a dull green fruit, with a slightly offset stem but no neck and with numerous elevated surface spots of a light green color.

It differs from the Anaheim in that the latter has no prominent neck and the stem is symmetrical. My new variety is decidedly richer in oil content than the Anaheim and the fruit does not attain such a large size as the Anaheim does. While the Anaheim tree is a slender, upright growing tree, my new variety is symmetrical in growth.

It differs from the Itzamna in that the latter produces a fruit with an even more prominent neck, with a hard shell and a mealy flesh.

It differs from the Edranol in that its fruit is smooth and glossy and that the tree is not of the slender upright growing type such as the Edranol.

It differs from the Hellen in that the fruit of the latter has a pebbled appearance and also that it matures in late summer and early fall. My new variety matures in early summer.

It differs from the Hass by its color and smoothness.

It differs from the Dickinson by its color, shape, smoothness, and skin, the latter being dark purple, oval, rough with a hard shell.

It differs from the Blake by its ripening season. The Blake ripens from October to December and is a Mexican type.

It differs from the Duke by its ripening season. The Duke ripens in October and November, is of Mexican type, and its crushed leaves have an anise-like odor. My new variety is a hybrid and its crushed leaves have no anise odor.

Having thus described my invention, I claim:

The avocado variety herein disclosed characterized by the tree's medium upright growing habit, blossoming in late spring with large, loose clusters of blossoms and producing a green, approximately eleven ounce fruit on an offset stem, the fruit having a glossy external appearance, a flesh of buttery texture.

PAUL L. KOVACH.